United States Patent
Kinser

(10) Patent No.: US 10,376,193 B2
(45) Date of Patent: Aug. 13, 2019

(54) EMBEDDED SACRIFICIAL LAYER TO ENHANCE BIOSENSOR STABILITY AND LIFETIME FOR NANOPATTERNED ELECTRODES

(71) Applicant: International Business Machines Corporation, Armonk, NY (US)

(72) Inventor: Emily R. Kinser, Poughkeepsie, NY (US)

(73) Assignee: International Business Machines Corporation, Armonk, NY (US)

( * ) Notice: Subject to any disclaimer, the term of this patent is extended or adjusted under 35 U.S.C. 154(b) by 291 days.

(21) Appl. No.: 15/218,550

(22) Filed: Jul. 25, 2016

(65) Prior Publication Data

US 2018/0020957 A1  Jan. 25, 2018

(51) Int. Cl.
*A61B 5/1486* (2006.01)
*A61B 5/145* (2006.01)

(52) U.S. Cl.
CPC ........ *A61B 5/1486* (2013.01); *A61B 5/14532* (2013.01)

(58) Field of Classification Search
CPC ............................ A61B 5/1486; A61B 5/1473
See application file for complete search history.

(56) References Cited

U.S. PATENT DOCUMENTS

| | | |
|---|---|---|
| 2,933,458 A | 4/1960 | King et al. |
| 6,359,444 B1 | 3/2002 | Grimes |
| D469,540 S | 1/2003 | Holker et al. |
| 6,914,279 B2 | 7/2005 | Lu et al. |
| 7,005,048 B1 | 2/2006 | Watanabe et al. |
| 7,294,910 B2 | 11/2007 | Thomas et al. |
| 7,524,408 B2 | 4/2009 | Monbouquette et al. |
| 7,604,592 B2 | 10/2009 | Freeman et al. |
| 7,627,938 B2 | 12/2009 | Kim et al. |
| 7,894,914 B2 | 2/2011 | Stahmann et al. |
| 7,949,382 B2 | 5/2011 | Jina |
| 7,955,483 B2 | 6/2011 | Gu et al. |
| 8,076,125 B2 | 12/2011 | McGimpsey |
| 8,097,926 B2 | 1/2012 | De Graff et al. |
| 8,221,822 B2 | 7/2012 | Flanagan et al. |

(Continued)

FOREIGN PATENT DOCUMENTS

| | | |
|---|---|---|
| CN | 1598694 A | 3/2005 |
| CN | 106094426 A | 11/2016 |
| KR | 1020160092635 A | 8/2016 |

OTHER PUBLICATIONS

Carmo et al. "Bulk Metallic Glass Nanowire Architecture for Electrochemical Applications." ACS Nano. Apr. 26, 2011;5(4):2979-83. Epub Mar. 3, 2011.*

(Continued)

*Primary Examiner* — Meredith Weare
(74) *Attorney, Agent, or Firm* — Scully, Scott, Murphy & Presser, P.C.; Steven J. Meyers

(57) ABSTRACT

An electrode structure is provided that includes an electrode base having topography located on a surface of the electrode base structure. A biological functionalization layer is located on one or more exposed surfaces of at least the topography of the electrode. A sacrificial layer is located on the biological functionalization layer and is present at least in the physical space located between the individual features of the topography of the electrode.

18 Claims, 3 Drawing Sheets

(56) References Cited

U.S. PATENT DOCUMENTS

| | | | |
|---|---|---|---|
| 8,529,835 B2 | 9/2013 | Kaplan et al. | |
| 8,668,978 B2 | 3/2014 | Malima et al. | |
| 8,741,380 B2 | 6/2014 | Yoshida et al. | |
| 8,772,228 B2 | 7/2014 | Stupp et al. | |
| 8,808,516 B2 | 8/2014 | Melosh et al. | |
| 8,907,384 B2 | 12/2014 | Pace et al. | |
| 2005/0269285 A1 | 12/2005 | Jung et al. | |
| 2007/0148653 A1 | 6/2007 | Yoshida | |
| 2009/0137423 A1* | 5/2009 | Higson | G01N 27/403 506/12 |
| 2009/0155800 A1 | 6/2009 | Hong et al. | |
| 2009/0243584 A1 | 10/2009 | Zhang et al. | |
| 2010/0006451 A1 | 1/2010 | Gordon et al. | |
| 2010/0066346 A1 | 3/2010 | Zhang et al. | |
| 2010/0310773 A1* | 12/2010 | Yoshida | B29C 33/3842 427/304 |
| 2010/0318193 A1 | 12/2010 | Desai et al. | |
| 2011/0027458 A1* | 2/2011 | Boock | A61B 5/14532 427/9 |
| 2011/0073475 A1* | 3/2011 | Kastanos | A61B 5/14532 204/403.01 |
| 2011/0091510 A1 | 4/2011 | Lele et al. | |
| 2011/0230735 A1 | 9/2011 | Wolfe et al. | |
| 2011/0233063 A1 | 9/2011 | Seki et al. | |
| 2011/0301716 A1 | 12/2011 | Sirivisoot et al. | |
| 2011/0319734 A1 | 12/2011 | Gottlieb et al. | |
| 2012/0218550 A1 | 8/2012 | O'Mahony | |
| 2013/0079608 A1 | 3/2013 | Miller et al. | |
| 2013/0150822 A1 | 6/2013 | Ross | |
| 2014/0230854 A1 | 8/2014 | Lopez et al. | |
| 2014/0238574 A1 | 8/2014 | Kinser et al. | |
| 2016/0331290 A1* | 11/2016 | Oh | A61B 5/14865 |
| 2017/0209079 A1* | 7/2017 | Kinser | A61B 5/1486 |

OTHER PUBLICATIONS

List of IBM Patents or Patent Applications Treated as Related dated May 18, 2017, 2 pages.

Padmanabhan, J., et al., "Engineering Cellular Response Using Nanopatterned Bulk Metallic Glass", American Chemical Society Nano, Apr. 2014, pp. 4366-4375, vol. 8, No. 5.

S.-H. Parng, et al. "Effect of temperature and glucose concentration on a glass-based sensor for long-term stability investigation", J. Micro/Nanolith. MEMS MOEMS, Jan.-Mar. 2011, pp. 013003-1 to 013003-5, vol. 10(1).

J. Gajdzik, et al., "Enzyme immobilisation on self-organised nanopatterned electrode surfaces", Phys. Chem. Chem. Phys., Sep. 2010, pp. 12604-12607, 12.

D. C. Deshpande, et al., "Development of a nanoscale heterostructured glucose sensor using modified microfabrication processes", J. Micro/Nanolith., Apr.-Jun. 2008, MEMS MOEMS, pp. 023005-1 to 023005-6, vol. 7(2).

Browne, D. J., et al., "Comparison of nucleation and growth mechanisms in alloy solidification to those in metallic glass crystallisation—relevance to modeling", Transactions of The Indian Institute of Metals, Aug.-Oct. 2009, pp. 409-412, vol. 62, Issues 4-5.

Pitt, E. B., et al., "Temperature dependence of the thermoplastic formability in bulk metallic glasses", Journal of Applied Physics, published online Aug. 23, 2011, 110, pp. 043518-1 to 043518-7.

Lee, S. H., et al., "Nanostructured indium-tin-oxide films fabricated by all-solution processing for functional transparent electrodes", Optics Express, Oct. 2011, pp. 21803-21808, col. 19, No. 22.

Kaushik, N., et al., "Metallic glass thin films for potential biomedical applications," Journal of Biomedical Materials Research B: Applied Biomaterials, Oct. 2014, pp. 1544-1552, vol. 102B, Issue 7.

Office Action dated Apr. 6, 2018 received in U.S. Appl. No. 15/005,690.

International Search Report dated May 14, 2018 received in a related foreign application.

Mailoa, J. P., et al., "Textured Conducting Glass by Nanosphere Lithography for Increased Light Absorption in Thin-Film Solar Cells", J. Phys. D. Appl. Phys., Feb. 2014, 6 pages, vol. 47, No. 8, 058105.

Office Action dated Jan. 31, 2018 received in U.S. Appl. No. 15/005,690.

Notice of Allowance dated Oct. 11, 2018 received in U.S. Appl. No. 15/005,690.

Crystallography365, "GOLD! The crystal structure of success", posted on Jan. 17, 2014, 4 pages.

Notice of Allowance dated Aug. 14, 2018 received in U.S. Appl. No. 15/419,524.

Zhai, D., et al., "Highly Sensitive Glucose Sensor Based on Pt Nanoparticle/Polyaniline Hydrogel Heterostructures", ACS Nano, Publication Date (Web): Mar. 11, 2013, pp. 3540-35467 (4).

Freckmann, G., et al.,"System Accuracy Evaluation of 27 Blood Glucose Monitoring Systems According to DIN EN ISO 15197", Diabetes Technology & Therapeutics. Mar. 2010, pp. 221-231, vol. 12, No. 3.

Cardosi, M., et al., "Amperometric glucose sensors for whole blood measurement based on dehydrogenase enzymes", Biochemistry, Genetics and Molecular Biology "Dehydrogenases", INTECH Open Access Publisher, Nov. 2012, Chapter 13, pp. 320-354.

* cited by examiner

EMBEDDED SACRIFICIAL LAYER TO ENHANCE BIOSENSOR STABILITY AND LIFETIME FOR NANOPATTERNED ELECTRODES

BACKGROUND

The present application relates to a biosensor structure and a method of forming the same. More particularly, the present application relates to a structure containing a nanopatterned biosensor electrode which includes an embedded sacrificial layer deposed between the nanopatterned features of the electrode, which may dissolve/biodegrade over time and during use in biosensing applications.

Biosensors with enhanced signal and sensitivity are essential to provide reliable data for both medical and environmental monitoring. Such biosensors are especially needed for areas related to food and water supply security as well as the healthcare industry. For healthcare, glucose sensors comprise a significant portion of the existing biosensor market. Platinum (Pt) is commonly used as a working electrode in glucose sensors, and platinum has demonstrated biocompatibility. Electrochemical sensors for external use (so-called "Test-Strips") are commonly used for glucose monitoring applications. However, limitations exist on the accuracy and applicability of test strip sensors.

In vivo glucose sensors, which are implanted into a human body, can be used to continuously monitor blood sugar. However, the foreign body response restricts in vivo biosensors. Moreover, the foreign body response can reduce the sensor signal output over time.

Despite advances made in biosensor technology, there is still a need to provide low-cost biosensors that exhibit enhanced sensor signal and sensitivity, and which may also mitigate the foreign body response.

SUMMARY

In one aspect of the present application, a structure that can be used as a bio sensor is provided. In one embodiment of the present application, the structure includes an electrode having topography located on a surface of an electrode base structure. A biological functionalization layer is located on one or more exposed surfaces of at least the topography of the electrode. A sacrificial layer is located on the biological functionalization layer and is present in the physical space or gaps located between the individual features of the topography of the electrode. The sacrificial layer is a biodegradable material that dissolves over time and during standard sensing applications.

In another aspect of the present application, a method of forming a structure that can be used as a biosensor is provided. In one embodiment of the present application, the method may include providing an electrode having topography located on a surface of an electrode base structure. Next, a biological functionalization layer is attached to one or more exposed surfaces of at least the topography of the electrode. A sacrificial layer is then formed on the exposed surface of the biological functionalization layer and within gaps or physical spaces located between individual features of the topography of the electrode. The sacrificial layer is a biodegradable material that dissolves over time and during sensing applications.

DETAILED DESCRIPTION

Figure 1:
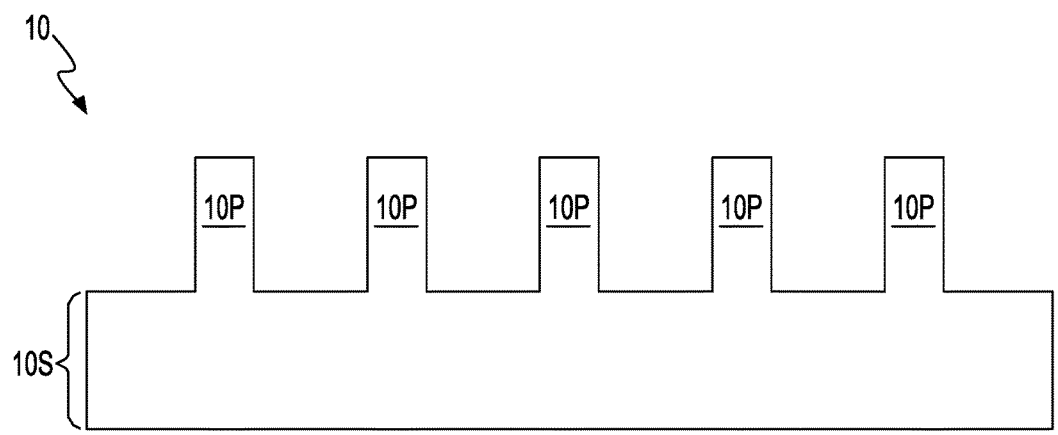
FIG. 1 is a cross sectional view of an exemplary structure including an electrode having non-random topography located on one surface of an electrode base structure, wherein the electrode base structure and the non-random topography are of uniform construction and uniform composition.

The present application will now be described in greater detail by referring to the following discussion and drawings that accompany the present application. It is noted that the drawings of the present application are provided for illustrative purposes only and, as such, the drawings are not drawn to scale. It is also noted that like and corresponding elements are referred to by like reference numerals.

In the following description, numerous specific details are set forth, such as particular structures, components, materials, dimensions, processing steps and techniques, in order to provide an understanding of the various embodiments of the present application. However, it will be appreciated by one of ordinary skill in the art that the various embodiments of the present application may be practiced without these specific details. In other instances, well-known structures or processing steps have not been described in detail in order to avoid obscuring the present application.

It will be understood that when an element as a layer, region or substrate is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "beneath" or "under" another element, it can be directly beneath or under the other element, or intervening elements may be present. In contrast, when an element is referred to as being "directly beneath" or "directly under" another element, there are no intervening elements present.

At present, the primary factor limiting the viable lifetime of implanted electrochemical glucose biosensors for continuous monitoring is the inflammatory foreign body response (FBR). Beyond the sensor's limitations to FBR, a secondary limitation to sensor functional lifetime is the ability of the electrode to transduce the chemical signal associated with the glucose reaction byproducts to an electrical signal that represents the glucose concentration. The majority of glucose biosensors utilize platinum, Pt, as an active electrode material, and silver/silver chloride, Ag—AgCl, as a reference electrode. Over time, the enzyme coating functionalization layer that is required as a catalyst for the red-ox reaction of glucose may be depleted, or development of surface layers occurs on the enzymes and the electrode material which effectively restricts access of biological fluids to the electrode surface and therefore corresponds with a reduction in electrochemical reaction and sensor signal. In order to develop an in vivo electrochemical biosensor that remains viable for timeframes exceeding conventional Pt-based biosensors mentioned above (which is usually on the order of a week), improvements to the electrode sensitivity over sustained periods are required.

The present application provides an electrode that can overcome problems associated with prior art biosensors, such as the Pt-based biosensors mentioned above. In the present application, an electrode structure is provided that includes an electrode having topography located on one surface of electrode base structure. In some embodiments the topography is non-random. In some embodiments, the electrode base structure and the topography of the electrode are of uniform construction and uniform composition. A biological functionalization layer is located on exposed surfaces of at least the topography. The biological functionalization material may optionally cover the entirety of a topmost exposed surface of the electrode base structure in addition to exposed surface area of the individual features of the topography. A sacrificial layer is located on the biological functionalization layer and is present at least in gaps or physical spaces located between the individual features of the topography of the electrode. The sacrificial layer is a biodegradable material which can be dissolved at a known rate to maintain or enhance sensor signal and sensitivity in vivo in order to increase the stability of the overall sensor performance and the extend the biosensor's useful lifetime in vivo.

Referring first to FIG. 1, there is illustrated an exemplary structure that can be employed in the present application. The exemplary structure of FIG. 1 includes an electrode 10 having non-random topography (collectively defined by the non-random i.e., regular repeating, individual articulated features 10P) located on one surface of an electrode base structure 10S, wherein the electrode base structure 10S and the non-random topography are of uniform construction and uniform composition. That is, the electrode 10 shown in FIG. 1 does not include an interface between the electrode base structure 10S and the non-random i.e., regular repeating, individual articulated features 10P that collectively define the non-random topography of electrode 10. Although the present application specifically describes and illustrates the electrode 10 shown in FIG. 1, the present application can work with any electrode having topography (random or non-random) located on a surface of an electrode base structure.

The shape of the electrode base structure 10S is not limited to any specific shape. In one embodiment of the present application, the shape of the electrode base structure 10S is a polygonal. In such an embodiment, the shape of the electrode base structure 10S may be triangular, quadrilateral or pentagonal. In other embodiments, the shape of the electrode base structure 10S may be circular or elliptical. The shape of the electrode base structure 10S may also include additional structures such as wiring or probe pads required to read out the electrical signal from the electrode 10.

Each non-random individual articulated feature 10P that provides the non-random topography of the electrode 10 has a size that is less than the size of the electrode base structure 10S. Each non-random individual articulated feature 10P may have various shapes and sizes. For example, each non-random individual articulated feature 10P may have a shape of a rod, a cone, an ellipse, or an annular structure. In one embodiment of the present application, each non-random individual articulated feature 10P may have a critical dimension ranging in size from 5 nm to 900 nm. In another embodiment of the present application, each non-random individual articulated feature 10P may have a critical dimension ranging in size from 20 nm to 300 nm. In one embodiment of the present application, each non-random individual articulated feature 10P has a pitch ratio of from 2:1 to 100:1. In another embodiment of the present application, each non-random individual articulated feature 10P has a pitch ratio of from 2:1 to 20:1.

In one embodiment of the present application, each non-random individual articulated feature 10P has a height from 5 nm to 300 µm. In another embodiment of the present application, each non-random individual articulated feature 10P has a height from 50 nm to 20 µm. In one embodiment of the present application, each non-random individual articulated feature 10P has an aspect ratio (i.e., ratio of width to height) of 1:1 to 500:1. In another embodiment of the present application, each non-random individual articulated feature 10P has an aspect ratio (i.e., width to height) of 2:1 to 100:1.

As mentioned above, the electrode base structure 10S and each non-random individual articulated feature 10P that provides the non-random topography of the electrode 10 are of unitary construction (i.e., single piece) and of a same composition. Thus, in the preferred embodiment, the electrode 10 of the present application lacks an interface between the electrode base structure 10S and the non-random topography provided by the repeating individually articulated features 10P. In an alternate embodiment, the electrode may be formed of the same composition in a construction which features an interface between the topography elements and the base electrode structure. In yet another embodiment, the topography elements and the base electrode structure may be comprised of different materials which may result in an interface.

The electrode 10 of the present application including the electrode base structure 10S and each non-random individual articulated feature 10P that provides the non-random topography of the electrode 10 are composed of an electrically conductive material (hereinafter just "conductive material"). In one embodiment of the present application, the electrode 10 is composed of a metallic glass. By "metallic glass" it is meant a solid metallic material, usually an alloy, with a disordered amorphous atomic structure. Metallic glasses can also be referred to herein as amorphous metals or glassy metals. In the case where the conductive material that provides the electrode 10 is a metallic glass, the conductive material can be non-crystalline or amorphous. In some embodiments, the metallic glass that can be used as the conductive material that provides electrode 10 of the present application may include an element selected from platinum, copper, nickel, phosphorous, palladium, zirconium, silver, aluminum, carbon or alloy or alloys thereof. In one example, the electrode 10 is composed of a platinum-based bulk metallic glass alloy such as, but not limited to, a PtCuNiP alloy.

In some embodiments, the conductive material that provides the electrode 10 is a conductive metal-containing material including, but not limited to, platinum, copper, silver, gold, tungsten, aluminum, iron, palladium, nickel, titanium, or zirconium. Alloys of these metals may also be employed as the conductive metal-containing material that can provide electrode 10.

The electrode 10 can be formed utilizing various techniques. In one embodiment of the present application, the electrode 10 may be formed by first providing a mold having a pattern that comprises both an electrode base shape and a nanotopography shape. By "nanotopography shape" is meant an array of non-random (i.e., regular repeating) individual articulated features whose size is less than the size of the electrode base substrate shape of the mold. The mold may be composed of any material including for example, a semiconductor material and/or a dielectric material. The mold may be formed by lithography and etching. A conductive material that provides the electrode 10 is then formed into the mold. In one embodiment, an amorphous metal, which may also be referred to as a "metallic glass" or a "bulk metallic glass," is introduced into the mold by utilizing a thermoplastic forming process to provide an electrode 10 comprising the amorphous metal (i.e., metallic glass) and having the electrode base substrate shape and the nanotopography shape resulting from the influence of the mold. In another embodiment, the conductive material that provides the mold may include a conductive metal-containing material as defined above that is electrodeposited on a surface of a metallic seed layer that is provided on the mold. After forming the conductive material into the mold and removing any excess conductive material formed outside of the mold, the mold is then removed from the resultant electrode 10 utilizing means well known to those skilled in the art.

In another embodiment, the electrode 10 can be formed by first providing an electrode structure comprising a conductive material. Thereafter, lithography and etching can be used to provide the electrode 10 with non-random topography shown in FIG. 1.

The electrode 10 illustrated in FIG. 1 can be used as a component in various biosensor configurations which include other well-known components, such as but not limited to, reference and counter electrode structures.

Figure 2:
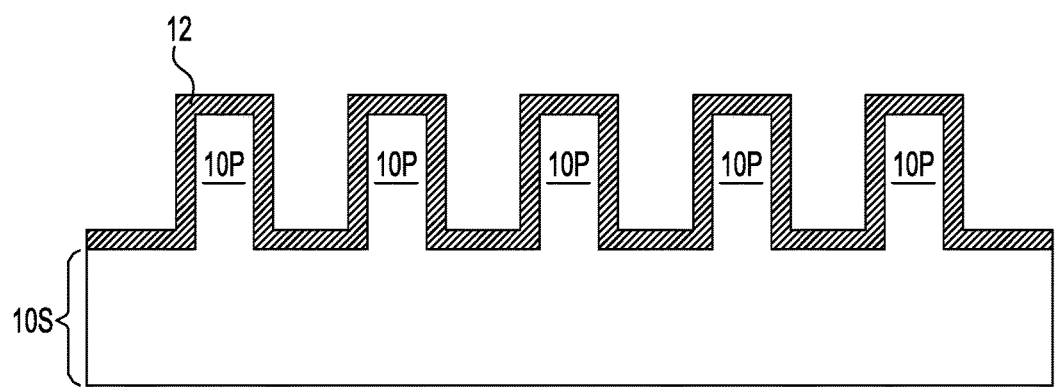
FIG. 2 is a cross sectional view of the exemplary structure of FIG. 1 after attaching a biological functionalization layer to exposed surfaces of at least the non-random topography of the electrode.

Referring now to FIG. 2, there is illustrated the exemplary structure of FIG. 1 after attaching a biological functionalization layer 12 to exposed surfaces of at least the non-random topography provided by the non-random individual articulated features 10P of the electrode 10. In one embodiment, and as shown, the biological functionalization layer 12 is attached, i.e., formed, on the exposed sidewall surfaces and topmost surface of the non-random topography provided by the non-random individual articulated feature 10P of the electrode 10. As is shown, a bottom-most surface of the biological functionalization layer 12 is located on a portion of a top-most exposed surface of the electrode non-random topography 10P of the electrode 10 of the present application. In yet another embodiment (not shown), but readily understood by those skilled in the art, the biological functionalization layer 12 may extend and cover the entirety of the electrode base structure 10S of the electrode 10, in addition to covering the exposed surfaces of the non-random topography 10P.

By "biological functionalization layer" it is meant any bioreceptor that binds with a complementary target biomolecule to create a binding event. In the primary embodiment, biochemical reactions involving the biological functionalization material generate an electrical signal which can be conducted by the non-random individual articulated features 10P of the electrode 10 of the present application under an applied electric potential. Examples of biological functionalization materials that can be used in the present application include an oligonucleotide, a nucleic acid, a peptide, a ligand, a protein, an enzyme, or any other material apt to bind with a complementary target biomolecule. When the electrode 10 of the present application is used for glucose sensing, the biological functionalization layer 12 can be composed of glucose oxidase or glucose dehydrogenase.

The biological functionalization layer 12 can be applied to the electrode 10 of the present application utilizing established biological functionalization processes known to those skilled in the art. Such biological functionalization processes typically include a series of chemical reactions that attach the biological functionalization layer 12 on the surface of the electrode 10 of the present application. In some embodiments, block mask technology may be used to prevent the formation of the biological functionalization layer 12 across the entirety of the topmost surface of the electrode base structure 10S. Alternatively, a continuous biological functionalization layer may be formed and then lithography and etching can be used to remove preselected portions of the biological functionalization layer from the topmost exposed surface of the electrode base 10S.

Figure 3:
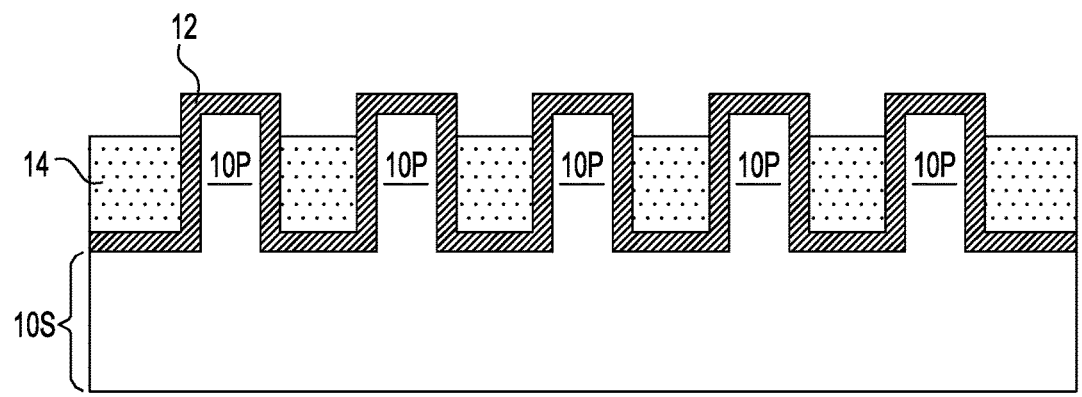
FIG. 3 is a cross sectional view of the exemplary structure of FIG. 2 after forming a sacrificial layer on the exposed surface of the biological functionalization layer and within physical spaces and gaps located between the individual features of the non-random topography of the electrode.

Referring now to FIG. 3, there is illustrated the exemplary structure of FIG. 2 after forming a sacrificial layer 14 on the biological functionalization layer 12 and within physical spaces or gaps located between the non-random topography defined by the non-random individual articulated features 10P of the electrode 10. The sacrificial layer 14 is a biodegradable material that dissolves over time and during sensing, particularly biosensing, applications. For example, the structure shown in FIG. 3 may be used in applications including sensing of various foods, water supplies as well as the healthcare industry. For healthcare, the structure shown in FIG. 3 may be used, for example, as a glucose sensor, including as an in vivo glucose sensor, which can be implanted into a human body, and which can be used to continuously monitor blood sugar.

The sacrificial layer 14 may be any polymer, metal, ceramic or nanoparticle that is biodegradable, compatible (e.g., non-toxic and non-harmful) for insertion into the human body, and that dissolves over time and during use in a particular sensing application. Examples of polymers that satisfy the above criteria and thus can be used as the sacrificial layer 14 include, but are not limited to, polyactide (PLA), polyglyocides (PGA), poly(lactic-co-glycolic acid) (PLGA), polycaprolatone (PCL), or other natural polymers. Examples of ceramics that satisfy the above criteria and thus can be employed as the sacrificial layer 14 include, but are not limited to, hydroxyapatite. Examples of metals that satisfy the above criteria and thus can be used as the sacrificial layer 14 include, but are not limited to, bulk metallic glasses (BMG) including Ca-based BMGs and Mg-based BMGs. In some embodiments and when BMGs are used as the sacrificial layer 14, the BMG that provides the sacrificial layer 14 is different in composition than that of the conductive material that provides the electrode 10. Examples of nanoparticles that satisfy the above criteria and thus can be employed as the sacrificial layer 14 include, but are not limited to, biodegradable nanoparticles formed utilizing the polymers, ceramics, and BMG materials previously described.

The sacrificial layer 14 may be formed utilizing various deposition processes including, for example, dip coating, sputtering, electroplating, chemical vapor deposition, plasma enhanced chemical vapor deposition, spin-on coating, or physical vapor deposition. In some embodiments, an etch back process may follow the deposition of the biodegradable material that provides the sacrificial layer 14. In some cases, a planarization process such as, for example, chemical mechanical planarization, may be performed between the depositing and etch back. In other embodiments, only a deposition process is used to form the sacrificial layer 14.

The sacrificial layer 14 has a topmost surface that can be either equal to, or less, than the topmost surface of the biological functionalization material 12 that is present on the topmost surface of each non-random individual articulated feature 10P that provides the non-random topography of the electrode 10. As shown, a topmost surface of the biological functionalization material 12 that is present on the topmost surface of each non-random individual articulated feature 10P that provides the non-random topography of the electrode 10 is exposed and thus is not covered by the sacrificial layer 14. Sacrificial layer 14 thus may be referred to herein as an "embedded" sacrificial material. Sacrificial layer 14 may completely, or partially, fill the gaps that are present between the non-random topography of the electrode 10.

In accordance with the present application, the sacrificial layer 14 can be dissolved/degraded at a known rate to maintain or, in some instances, enhance sensor signal and sensitivity in vivo. As such, the sacrificial layer 14 can be used to increase the stability of the overall biosensor performance and/or to extend the biosensor useful lifetime in vivo.

FIG. 3 illustrates an exemplary structure of the present application. The exemplary structure includes an electrode 10 having non-random topography (defined by the non-random individual articulated features 10P) located on one surface of an electrode base structure 10S, wherein the electrode base structure 10S and the non-random topography (defined by the non-random individual articulated features 10P) are of uniform construction and uniform composition. A biological functionalization layer 12 is located on exposed surfaces of at least the non-random topography (defined by the non-random individual articulated features 10P) of the electrode 10. A sacrificial layer 14 is located on the top exposed surface of the biological functionalization layer 12 and is present in physical spaces or gaps located between the non-random topography (defined by the non-random individual articulated features 10P) of the electrode 10. The sacrificial layer 14 is a biodegradable material that dissolves over time and during sensing applications.

Figure 4:
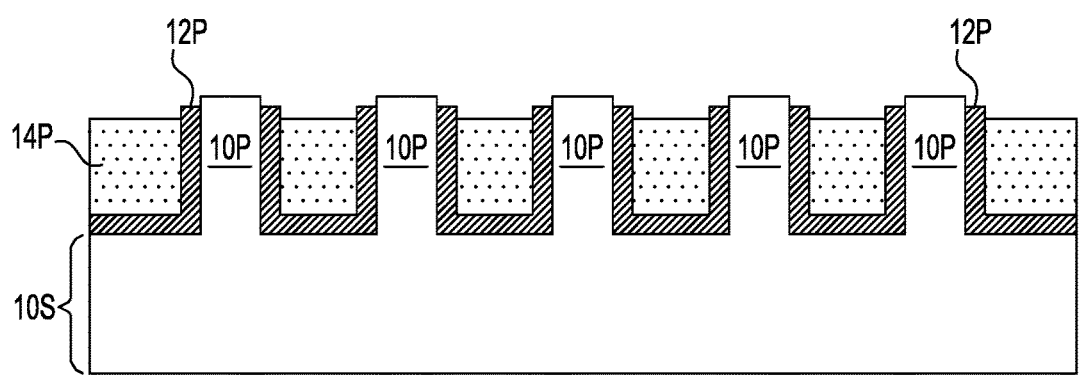
FIG. 4 is a cross sectional view of the exemplary structure of FIG. 3 after using the structure for a first period of time and during a biosensing application.

Referring now to FIG. 4, there is illustrated the exemplary structure of FIG. 3 after using the structure for a first period of time and during a biosensing application, such as, for example, monitoring blood sugar. As is shown, and during the course of use, the sacrificial layer 14 of the exemplary structure shown in FIG. 3 dissolves/degrades to expose fresh and undepleted portions of the biological functionalization layer 12 (labeled as 12P in FIG. 4) that were previously covered by the sacrificial layer 14. In FIG. 4, element 14P denotes the sacrificial layer 14 that remains after this first period of time. Each remaining sacrificial layer 14 after the first period of time can be referred to herein as sacrificial layer portion 14P. The dissolving/degrading of the sacrificial layer 14 provides increased electrode area to enhance sensitivity of the biosensor in order to compensate for decreased access of biological fluids over time due to foreign body response or maintain sensitivity over extended in vivo biosensor life time which may result in the depletion or consumption of the exposed biological functionalization layer.

Figure 5:
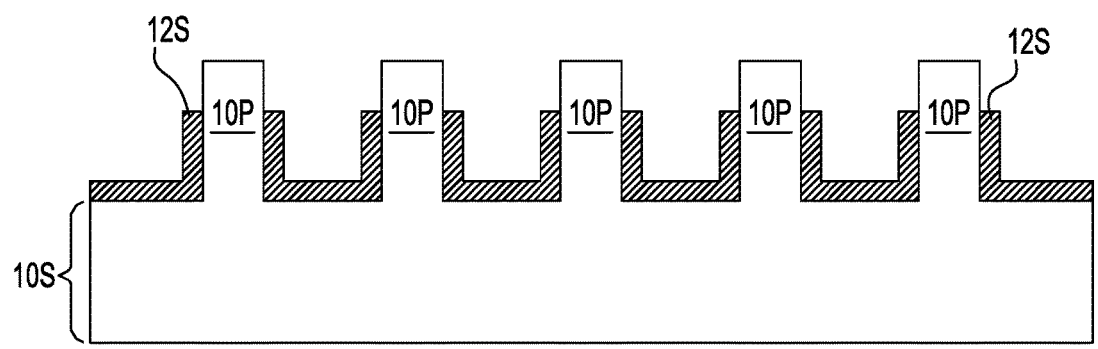
FIG. 5 is a cross sectional view of the exemplary semiconductor structure of FIG. 4 after the end of the lifetime of the structure.

Referring now to FIG. 5, there is shown the exemplary semiconductor structure of FIG. 4 after the end of the lifetime of the structure. As is shown, and at the end of the sensor useful life, the sacrificial layer 14 is completely removed such that the active sensor area provides comparable signal and sensitivity as at the beginning of use of the sensor. In FIG. 5, element 12S denotes remaining portions of the biological functionalization layer 12 as the end of the sensors useful life.

While the present application has been particularly shown and described with respect to preferred embodiments thereof, it will be understood by those skilled in the art that the foregoing and other changes in forms and details may be made without departing from the spirit and scope of the present application. It is therefore intended that the present application not be limited to the exact forms and details described and illustrated, but fall within the scope of the appended claims.

What is claimed is:

1. A structure comprising:
an electrode having topography located on a surface of an electrode base structure, wherein said topography is defined by individual articulated features;
a biological functionalization layer located on one or more surfaces of at least said topography of said electrode; and
a sacrificial layer located on said biological functionalization layer and present only in the physical space located between said individual articulated features of said topography of said electrode such that the biological functionalization layer located on a topmost surface of said topography of said electrode is physically exposed.

2. The structure of claim 1, wherein said topography is non-random.

3. The structure of claim 2, wherein said electrode base structure and said non-random topography are of uniform construction and uniform composition.

4. The structure of claim 3, wherein said uniform composition of said electrode base structure and said non-random topography comprise a conductive material.

5. The structure of claim 4, wherein said conductive material is amorphous.

6. The structure of claim 4, wherein said conductive material comprises a metallic glass, wherein said metallic glass includes an element selected from the group consisting of platinum, copper, nickel, phosphorous, palladium, zirconium, silver, aluminum, carbon and an alloy of one or more of said elements.

7. The structure of claim 1, wherein each individually articulated feature comprises rods, cones, or annular structures.

8. The structure of claim 1, wherein said biological functionalization layer is composed of an oligonucleotide, a nucleic acid, a peptide, a ligand, a protein, an enzyme, or any other material apt to bind with a complementary target biomolecule.

9. The structure of claim 8, wherein said biological functionalization layer is composed of glucose oxidase or glucose dehydrogenase.

10. The structure of claim 1, wherein said sacrificial layer is composed of a biodegradable material.

11. The structure of claim 10, wherein said biodegradable material is selected from the group consisting of a polymer, a metal, a ceramic or nanoparticles.

12. The structure of claim 1, wherein a portion of said biological functionalization material is present on an exposed surface of said electrode base structure.

13. A method of forming a structure, said method comprising:

providing an electrode having topography located on a surface of an electrode base structure, wherein said topography is defined by individual articulated features;

attaching a biological functionalization material to one or more surfaces of at least said topography of said electrode; and forming a sacrificial layer on said biological functionalization layer and only within gaps located between said individual articulated features of said topography of said electrode such that the biological functionalization layer located on a topmost surface of said topography of said electrode is physically exposed.

14. The method of claim 13, wherein said topography is non-random.

15. The method of claim 14, wherein said electrode base structure and said non-random topography are of uniform construction and uniform composition.

16. The method of claim 13, wherein said forming said sacrificial layer comprises:
   depositing a biodegradable material; and
   performing a recess etch.

17. The method of claim 13, wherein each individually articulated feature comprises rods, cones, or annular structures.

18. The method of claim 13, wherein said sacrificial layer is composed of a biodegradable material.

* * * * *